(12) United States Patent
Kema et al.

(10) Patent No.: US 11,280,802 B2
(45) Date of Patent: Mar. 22, 2022

(54) METHODS AND KITS FOR THE DERIVATIZATION OF A BIOGENIC AMINE

(71) Applicants: Rijksuniversiteit Groningen, Groningen (NL); Academisch Ziekenhuis Groningen, Groningen (NL)

(72) Inventors: Ido Peter Kema, Eelde (NL); Claude Pascal Van Der Ley, Gieten (NL); Hermannus Johannes Roelof Van Faassen, Lutten (NL)

(73) Assignees: Academisch Ziekenhuis Groningen, Groningen (NL); Rijksuniversiteit Groningen, Groninigen (NL)

( * ) Notice: Subject to any disclaimer, the term of this patent is extended or adjusted under 35 U.S.C. 154(b) by 119 days.

(21) Appl. No.: 16/304,376

(22) PCT Filed: May 24, 2017

(86) PCT No.: PCT/NL2017/050332
§ 371 (c)(1),
(2) Date: Nov. 26, 2018

(87) PCT Pub. No.: WO2017/204637
PCT Pub. Date: Nov. 30, 2017

(65) Prior Publication Data
US 2019/0170776 A1   Jun. 6, 2019

(30) Foreign Application Priority Data
May 26, 2016   (EP) .................... 16171512

(51) Int. Cl.
*G01N 33/68*   (2006.01)
*G01N 33/94*   (2006.01)

(52) U.S. Cl.
CPC ..... *G01N 33/9406* (2013.01); *G01N 33/6812* (2013.01); *G01N 33/6848* (2013.01); *G01N 33/94* (2013.01); *G01N 2560/00* (2013.01); *Y10T 436/173845* (2015.01); *Y10T 436/24* (2015.01)

(58) Field of Classification Search
CPC .......... G01N 2560/00; G01N 33/6812; G01N 33/6848; G01N 33/94; G01N 33/9406; G01N 33/48; Y10T 436/17; Y10T 436/173845; Y10T 436/20; Y10T 436/200833; Y10T 436/201666; Y10T 436/203332; Y10T 436/24; Y10T 436/25; Y10T 436/25375

USPC ........ 436/63, 106, 111, 127, 128, 129, 131, 436/161, 173, 174, 177
See application file for complete search history.

(56) References Cited

U.S. PATENT DOCUMENTS

| | | | | |
|---|---|---|---|---|
| 4,908,322 A | * | 3/1990 | Jacobson | G01N 33/52 436/106 |
| 5,011,608 A | * | 4/1991 | Damjanovic | B01D 15/08 210/198.2 |
| 9,146,219 B2 | * | 9/2015 | Yue | G01N 33/9406 |
| 10,267,775 B2 | * | 4/2019 | Huang | G01N 1/405 |

FOREIGN PATENT DOCUMENTS

WO   2008094043 A2   8/2008

OTHER PUBLICATIONS

Zhang et al. Journal of Pharmaceutical and Biomedical Analysis, vol. 117, Sep. 5, 2015, pp. 227-231.*
Hiemke, C. et al., "Gas-Liquid Chromatographic Properties of Catecholamines, Phenylethylamines and Indolalkylamines as Their Propionyl Derivatives", Journal of Chromatography, 153, (1978) 451-460.
Ford, Q.L. et al., "Aqueous in situ derivatization of carboxylic acids by an iconic carbodiimide and 2,2,2-trifluoroethylamine for electron-capture detection", Journal of Chromatography A, 1145 (2007) 241-245.
Bourgogne, E. et al., "Simultaneous quantitation of histamine and its major metabolite 1-methylhistamine in brain dialysates by using precolumn derivatization prior to HILIC-MS/MS analysis", Anal. Bioanal. Chem. (2012) 402: 449-459.

* cited by examiner

Primary Examiner — Maureen Wallenhorst
(74) Attorney, Agent, or Firm — Verrill Dana, LLP

(57) ABSTRACT

A method for the in situ derivatization of at least one biogenic amine, precursor, or metabolite thereof in an isolated aqueous sample includes the steps of: (i) contacting the sample with a propionic anhydride/acetonitrile solution in the presence of a phosphate buffer having a pH in the range of 7.0 to 9.0 and allowing the conversion of amine and/or hydroxyl moieties of the biogenic amine, precursor, or metabolite thereof to form a propionyl derivative of the biogenic amine; followed by (ii) adding to the reaction mixture obtained in step (i) a carbodiimide compound and an electrophilic amine-containing compound, and allowing the carbodiimide-mediated derivatization of carboxylic acid moieties of the biogenic amine, precursor, or metabolite thereof.

16 Claims, 5 Drawing Sheets

METHODS AND KITS FOR THE DERIVATIZATION OF A BIOGENIC AMINE

Figures 1A, 1B:
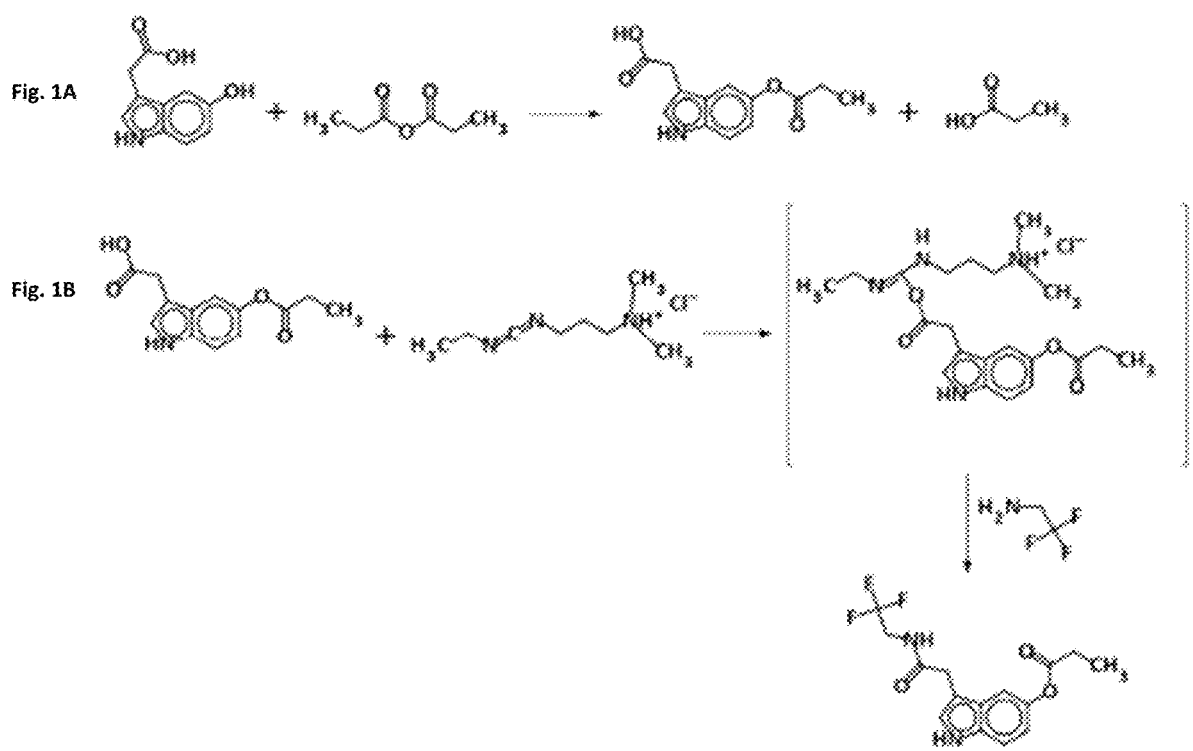

The invention relates to analytical chemistry, in particular to means and methods for the quantitative determination of derivatized biogenic amines, precursors or metabolites thereof.

A biogenic amine is a biogenic substance with one or more amine groups. They are basic nitrogenous compounds formed mainly by decarboxylation of amino acids or by amination and transamination of aldehydes and ketones. Biogenic amines are organic bases with low molecular weight and are synthesized by microbial, vegetable and animal metabolisms. Some prominent examples of biogenic amines include classical monoamines like histamine, serotonin and catecholamine neurotransmitters. Histamine is a substance derived from the amino acid histidine that acts as a neurotransmitter mediating arousal and attention, as well as a pro-inflammatory signal released from mast cells in response to allergic reactions or tissue damage. Histamine is also an important stimulant of HCl secretion by the stomach through histamine H2 receptors. Serotonin is a central nervous system neurotransmitter derived from the amino acid tryptophan involved in regulating mood, sleep, appetite, and sexuality. The catecholamine norepinephrine (noradrenaline) is a neurotransmitter involved in sleep and wakefulness, attention, and feeding behavior, as well as a stress hormone released by the adrenal glands that regulates the sympathetic nervous system. Epinephrine (adrenaline) is an adrenal stress hormone, as well as a neurotransmitter present at lower levels in the brain. Dopamine is a neurotransmitter involved in motivation, reward, addiction, behavioral reinforcement, and coordination of bodily movement.

Since biogenic amines like catecholamines have an important function in the homeostasis of the organism as a neurotransmitter, their kinetic analysis in vivo has become a major research challenge. However, biogenic amines and their metabolites in biological fluids are present at low endogenous concentrations.

Recent attempts have been made to analyze pharmacologically relevant biogenic monoamines and amino acids in liquid chromatography—tandem mass spectrometry, or LC-MS-MS. This is an analytical technique which combines high selectivity with high sensitivity. Generally, in LC-MS-MS, a mixture of analytes is first separated on a column using liquid chromatography (LC). The one or more (derivatized) analytes which are eluting from the LC at a certain time are collected and transferred to the first MS. These processes commonly occur on-line. Herein, ionization of the one or more eluted analytes takes place, which ionization is commonly performed using atmospheric pressure chemical ionization (APCI) or Electron Spray Ionization (ESI) techniques. The corresponding one or more molecular ions thus formed are selected in the first MS. These molecular ions (which all have one m/z value but which may correspond to one or more different chemical identities) are then transferred into a collision chamber. In this chamber, the molecular ions disintegrate into characteristic fragments. One fragment which is characteristic for the analyte of interest, having one specific m/z value, is detected in the second MS. LC-MS-MS can be employed to quantitatively determine the analyte in a sample. One way to allow quantitation is by comparative analysis of accurately known concentrations of analytes. The great selectivity of MS-MS which involves the selection of two characteristic ions (one for the molecular ions comprising the molecular ions of the analyte (parent ion), one for an ion fragment which is uniquely characteristic for the analyte (product ion)) not only helps to distinguish the analyte from the other compounds in the sample, it also greatly assists in the accuracy and the reproducibility of the quantitative analysis.

Several biogenic amine derivatization strategies have been published or patented. See for example Zhao et al., 2015; Zhang et al. 2012; Van de Merbel et al. 2011; Tan et al., 2014 or Ford et al., 2007.

However, each of the known protocols needs tedious extraction involving liquid-liquid extraction or offline solid-phase extraction or evaporation before derivatization, or they only selectively target either amine groups or carboxylic acid groups. For example, the established derivatization method using the so-called SymDaQ reagent has the disadvantages that it only targets primary amine groups, the formed derivative is not stable and thus has to be analyzed directly. Furthermore, metabolite analysis by LC-MS/MS is often hampered by low sensitivity (unspecific water loss and/or ammonia loss). Reasons for this are (i) higher background noise in the lower mass range; (ii) unspecific product ions and/or (iv) no abundant product ions.

The present inventors therefore sought to improve HPLC mass spectrometric detection of biogenic amines and other low molecular weight molecules having a mass of <200 amu and containing primary, secondary amine groups, hydroxyl groups and/or carboxylic acids. Moreover, it was desired to develop a simple derivatization strategy that is applicable directly (i.e. in situ) in a an aqueous sample, in particular in complex biological fluid samples (plasma, saliva, urine, CSF, cell lysate, cell culture supernatant etc.) without the need for prior extraction of the compound(s) of interest.

It was found that the above goals could be met by the provision of a double derivatization method involving the derivatization of amine, hydroxyl and/or carboxylic acid groups, such that the complete metabolic pathway of e.g. the catecholamines can be analysed with high sensitivity and selectivity in one run. After derivatization, the vial can be placed in the analytical system and a (online)-SPE-LC-MS/MS procedure can be run. The formed derivatives show an intensive precursor ion and a very specific production ion pattern (high intensity products) with almost no loss in sensitivity. Sensitivity for the tested compounds lies in the range of picomolar concentrations, even when analyzing very small sample volumes of e.g. only 50 µL of sample. The formed derivative is stable and can be analyzed even weeks after formation without loss in sensitivity.

Accordingly, the invention provides a method for the in situ derivatization of at least one biogenic amine, metabolite and/or precursor thereof in an aqueous sample, the derivatization comprising the steps of:

(i) contacting said sample with a propionic anhydride/acetonitrile solution in the presence of a phosphate buffer having a pH in the range of 7.0 to 9.0, preferably pH 8.0 to 8.5, and allowing the conversion of amine and/or hydroxyl moieties of the biogenic amine or metabolite thereof to form a propionyl derivative of said biogenic amine; followed by (ii) adding to the reaction mixture obtained in step (i) a carbodiimide reagent and an electrophilic amine-containing compound, and allowing the carbodiimide-mediated derivatization of carboxylic acid moieties of the biogenic amine, metabolite and/or precursor thereof.

A method of the invention is not known or suggested in the art. Bourgogne et al. (Anal. and Bioanal. Chem. (2011) vol. 402, no. 1, pp. 449-459) disclose a method for the derivatization of a biogenic amine comprising a precolumn derivatization of histamine and 1-methylhistamine in brain dialysates using propionic anhydride prior to (HILIC)-MS/

MS analysis. The derivatized sample is subjected to an extraction step before injecting it into the LC-MS/MS apparatus. However, Bourgogne et al. do not disclose a 2-step derivatization step as disclosed in the present invention, which allows the direct injection of a derivatized sample into the LC-MS/MS apparatus without further clean-up.

A biogenic amine is a biogenic substance with one or more amine groups. They are basic nitrogenous compounds formed mainly by decarboxylation of amino acids or by amination and transamination of aldehydes and ketones. According to the invention, the biogenic amine, metabolite and/or precursor thereof contains at least one or more primary, secondary amine groups, hydroxyl groups and/or carboxylic acids which is/are susceptible to the derivatization reactions. For example, the metabolite or precursor may be formed by an enzyme present in the metabolic pathway of tyrosine, tryptophan, histidine or arginine, or in the lysine degradation pathway (KEGG pathway). In one embodiment, the biogenic amine is a monoamine or polyamine that is involved in growth, renovation, and metabolism in organs and/or for high metabolic activity of the normal functioning and immunological system of the gut. In another embodiment, the biogenic amine can act as free radical scavenger or has antioxidants activity.

In yet another embodiment, the biogenic amine has a toxicological risk and induces adverse effects such as headaches, hypo- or hypertension, nausea, cardiac palpitation and even mortality in severe cases. When conditions that favor microbial or biochemical activity persist, biogenic amines are likely formed in food and beverages that contain proteins or free amino acids. Examples of such food and beverages include but not limited to fish, fish products, meat products (sausages), eggs, cheeses, fermented milk products, chocolate, nuts, fermented and fresh fruits, vegetables such as sauerkraut and soy bean products including soy sauce, beers and wines. Thus the presence and concentration of biogenic amines in food is thought to be related to spoilage and fermentation, particularly by microorganisms. Beer and wine are known to contain many different biogenic amines in various amounts and compositions. Histamine, tyramine, putrescine, isopentylamine and beta-phenylethylamine are some common biogenic amines found in wine.

Since biogenic amines can also serve as indicators of food spoilage caused by bacteria (i.e. to indirectly detect the presence of bacteria), the invention is advantageously used not only for detecting low levels of pharmacologically relevant amines, but also to derivatize and detect compounds that can serve as indicators of health complications, including cancer, bacterial infection, and food poisoning, to name a few. Food spoilage (e.g., meat and fish spoilage) occurs as bacteria begin to grow shortly after the time of slaughter. During the initial stages of food spoilage, free amino acids are decarboxylated by enzymes released by invading spoilage microorganisms. The product of decarboxylation includes biogenic amines, namely putrescine and cadaverine. These two amines are particularly distinctive in odor and correlate well with surface bacterial counts. Another product, histamine, is of interest due to its alleged ability to induce histamine intoxication, a form of food poisoning associated with the consumption of spoiled fish.

A method as herein disclosed is capable of discriminating analytes within the same or similar class of analytes.

As demonstrated herein below, a method of the invention is advantageously applied for the in situ derivatization of a biogenic amine neurotransmitter in a biological sample. Preferably, the biogenic amine is selected from the group consisting of epinephrine, norepinephrine, dopamine, serotonin, 5-hydroxyindolacetic acid (5-HIAA), metanephrine, normetanephrine and 3-methoxytyramine.

Other biogenic amines to be derivatized according to the invention include histamine, tyramine, beta-phenylethylamine, tryptamine, putrescine, cadaverine, spermine, spermidine, butylamine, dimethylamine, ethanolamine, ethylamine, hexylamine, indole, isopropylamine, isopentylamine, methylamine, 2-methylbutylamine, morpholine, pentylamine, piperidine, propylamine, pyrrolidine, spermidine and putrescine.

Exemplary precursors of biogenic amines include amino acids, such as histidine (histamine precursor), tyrosine (tyramine precursor), hydroxytryptophan (serotonin precursor), tryptophan (serotonin/tryptamine precursor), lysine (cadaverine precursor), ornithine (putrescine precursor) and arginine (precursor of agmatine, spermine, spermidine).

In one embodiment, the aqueous sample is an isolated biological sample, preferably selected from the group consisting of urine, plasma, saliva, CSF, cell lysate and cell culture supernatant. The sample is typically isolated from a mammalian subject, preferably a human subject. For example, the sample is a urinary sample from a patient at diagnosis or follow-up of a disease associated with aberrant levels of a biogenic amine, like catecholamine such as dopamine, norepinephrine or epinephrine.

Exemplary applications include:

(a) Plasma free or urinary fractionated metanephrines for pheochromocytoma diagnosis.

(b) Profile of tryptophan, 5-hydroxytryptophan, serotonin and 5-HIAA in platelet-rich-plasma for the diagnosis of neuroendocrine tumors.

(c) Detection of Catecholamines and acidic metabolites, serotonin and 5-HIAA (homovanillic acid, vanillylmandelic acid, 3-methoxy-4-hydroxyphenylglycol) in CSF and/or urine for detection of e.g. enzyme deficiencies (tyrosine hydroxylase, aromatic amino acid decarboxylase, dopamine beta-hydroxylase) neuroblastoma.

In another embodiment, the sample is a food sample, e.g. a food sample suspected to contain one or more biogenic amines that can cause health problems.

Figure 2A:
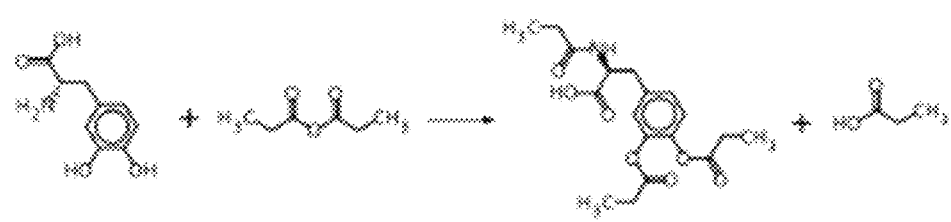

Step (i) of a method of the invention comprises contacting the aqueous sample with a propionic anhydride/acetonitril solution in the presence of a phosphate buffer having a pH in the range of 7.0 to 9.0. This step allows the conversion of amine and/or hydroxyl moieties of the biogenic amine or metabolite thereof to form a propionyl derivative. See FIGS. 1A and 2A for a schematic reaction. The alkaline phosphate buffer having a pH in the range of 7.0 to 9.0, preferably 7.5 to 8.8, more preferably 8.0 to 8.5, ensures that the conversion to a propionyl derivative takes place while it is not too alkaline to cause degradation of the biogenic amine. Typically, an incubation period of 5-60 minutes at room temperature is sufficient.

In one embodiment, the propionic anhydride/acetonitril solution is 10-50% v/v propionic anhydride in acetonitrile. Very good results were obtained with 20-30% v/v propionic anhydride in acetonitrile.

In a specific aspect, the pH of the phosphate buffer is in the range of 8.0 to 8.5. For example, a 0.5 M dipotassium phosphate buffer pH 8.5, optionally comprising 1-10 mM EDTA is suitably used.

Preferably, one or more internal standard(s) is added to the (biological) sample. An internal standard in analytical chemistry is a chemical substance that is added in a constant amount to samples, the blank and/or calibration standards in a chemical analysis. This substance can then be used for calibration by plotting the ratio of the analyte signal to the internal standard signal as a function of the analyte concentration of the standards. This is done to correct for the loss of analyte during sample preparation or sample inlet. The internal standard is typically a compound that is very similar, but not identical to the chemical species of interest in the samples, as the effects of sample preparation should, relative to the amount of each species, be the same for the signal from the internal standard as for the signal(s) from the species of interest in the ideal case. The person skilled in the art will be able to choose the appropriate internal standard(s) depending on the purpose and context of the derivatization method. Deuterated internal standards are particularly useful. For example, the standard is selected from the group consisting of L-DOPA-d3, dopamine-d4-HCl, norepinephrine-d6-HCl, serotonin-d4 creatinine sulfate, 5-Hydroxyindoleacetic acid (HIAA)-d2, epinephrine-d3, 3-methoxytyramine-d4-HCl, DL-metanephrine-d3-HCl, and DL-normetanephrine-d3-HCl.

In one embodiment, step (i) of a method of the invention comprises mixing 1 volume of (biological) sample, 1 volume of internal standard and 5 volumes of phosphate buffer, and contacting the mixture with 1 volume of propionic anhydride in acetonitrile.

Figure 2B:
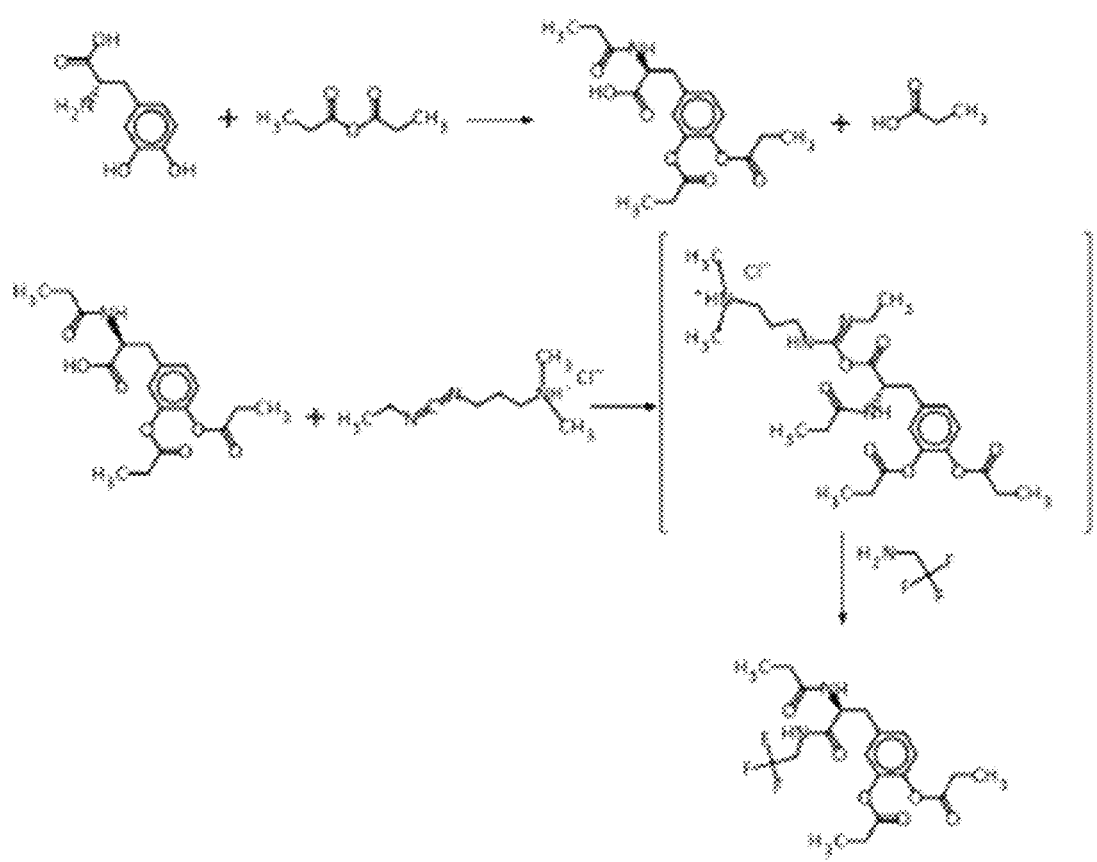

The conversion into propionyl derivative of the biogenic amine is directly followed by the second derivatization step by adding to the reaction mixture obtained in step (i) a carbodiimide reagent and a primary amine-containing compound, preferably an electrophilic amine-containing compound, and allowing the carbodiimide-mediated derivatization of carboxylic acid moieties of the biogenic amine, metabolite and/or precursor thereof. See FIGS. 1B and 2B for a schematic depiction of the reaction in step (ii). In one embodiment, step (ii) comprises adding 2 volumes of the carbodiimide reagent and 2 volumes of the amine-containing compound to 1 volume of the reaction mixture obtained in step (i). Preferably, about equimolar amounts of the carbodiimide reagent and the primary amine-containing compound are used.

Depending on the sample type, a volume of water may be added to dilute the reaction mixture of step (ii) such that the final concentration of the derivatized biogenic amine(s) is within a suitable range for detection. For example, in case of a urine sample, the concentration of biogenic amines is relatively high and several, e.g. 4-5 volumes of water are preferably added to prevent saturation of the MS detection signal. Incubation times for the second derivatization step typically range from about 10 to 60 minutes, preferably 20-40 minutes, at room temperature.

It was surprisingly observed that the carboxylic groups formed in the first derivatization step provide an acidic pH required for the second derivatization step, and thus no intermediate steps of sample purification, buffer change or the like is required.

Water-soluble carbodiimides have been used in the art as dehydrating agents for coupling carboxylic acids with amines to produce amide derivatives. The descriptive mechanism for carbodiimide-mediated derivatization is also known (see e.g. Ford et al. 2007). A given carboxylate and carbodiimide react to form an intermediate complex that is activated to attack by an electrophile such as an amine. Suitable water-soluble carbodiimide reagents for use in the present invention include N-ethyl-N'-(3-dimethylaminopropyl) carbodiimide (EDC) and 1-cyclohexyl-3-(2-morpholinoethyl)carbodiimide (CMC).

The primary amine-containing compound displaces the carbodiimide to generate the corresponding amide. The skilled person will appreciate that any electrophilic amine-containing compound can be used that can introduce a moiety allowing for a mass increase and improved signal-to-noise ratio. For example, by introducing halogen atoms or other moieties that do not naturally occur in the biogenic amines. Suitable amine-containing compounds include O-benzylhydroxylamine (O-BHA) and 2,2,2-trifluoroethylamine (TFEA). In a specific aspect, step (ii) comprises adding 2,2,2-trifluroethylamine (TFEA) and N-ethyl-N'-(3-climethylaminopropyl) carbodiimide (EDC). preferably 0.4 M TFEA and 0.4 M EDC.

Very good results are obtained when the (primary) amine-containing compound is added prior to the carbodiimide reagent, preferably with vortexing in between. For example, in one embodiment step (ii) comprises the addition of TFEA prior to EDC.

Following completion of step (ii), the method may involve a centrifugation step. For example, in case of a plasma sample derivatization the final reaction mixture is advantageously centrifuged and the resulting supernatant used for subsequent analysis.

A two-step derivatization method according to the invention is preferably followed by detecting at least one derivatized biogenic amine, for example by subjecting the derivatized sample to (in-line or off-line) SPE-LC-MS/MS or any other suitable analytical technique. In view of the high stability of the derivatives formed using a method as herein described, the detection need not take place directly after derivatization. In contrast, for practical and economical reasons it may be preferred to prepare and collect multiple (series of) derivatized samples on different days, and subject them to a detection step at a later point in time. For example, in one embodiment detection (e.g. using SPE-LC-MS/MS) is performed at least one week after derivatization.

In one embodiment, the detection step comprises ionizing the biogenic amine or metabolite thereof in a mass spectrometer by electrospray ionization to produce the protonated molecular ion of the biogenic amine or metabolite thereof; fragmenting the protonated molecular ion to produce a product ion, and detecting a presence or quantity of at least one of the protonated molecular ion or a product ion, wherein the presence or quantity of the detected ion is related to the presence or quantity of the biogenic amine or metabolite thereof in the biological sample.

A further aspect of the invention relates to a kit-of-parts for performing the in situ derivatization method according to the invention. The kit comprises at least (i) a first container comprising 10-50% v/v propionic anhydride in acetonitrile; (ii) a second container comprising a carbodiimide reagent, preferably N-ethyl-N'-(3-dimethylaminopropyl) carbodiimide (EDC) or 1-cyclohexyl-3-(2-morpholinoethyl)carbodiimide (CMC); and (iii) a third container comprising a primary amine-containing compound, preferably 2,2,2-trifluroethylamine (TFEA).

The kit may further comprising a phosphate buffer having a pH in the range of 7.0 to 9.0 and/or at least one biogenic amine internal standard.

Preferably, the internal standard is a deuterated standard. In one embodiment, the kit comprises one or more internal standards selected from the group consisting of L-DOPA-d3, dopamine-d4-HCl, norepinephrine-d6-HCl, serotonin-d4 creatinine sulfate, 5-HIAA-d2, epinephrine-d3, 3-methoxytyramine-d4-HCl, DL-metanephrine-d3-, and DL-normetanephrine-d3-HCl.

LEGEND TO THE FIGURES

FIG. 1. Schematic derivatization reaction in step (i) of a biogenic amine (in this case 5-HIAA) with propionic anhydride (panel A), and subsequently in step (ii) the derivatization of carboxylic acid moietie(s) of the biogenic amine with a carbodiimide reagent (here: EDC) and an electrophilic amine-containing compound (here: TFEA) (panel B).

FIG. 2. Schematic derivatization reaction in step (i) of a biogenic amine (in this case L-DOPA) with propionic anhydride (panel A), and subsequently in step (ii) the derivatization of carboxylic acid moietie(s) of the biogenic amine with a carbodiimide reagent (here: EDC) and an electrophilic amine-containing compound (here: TFEA) (panel B).

Figure 3:
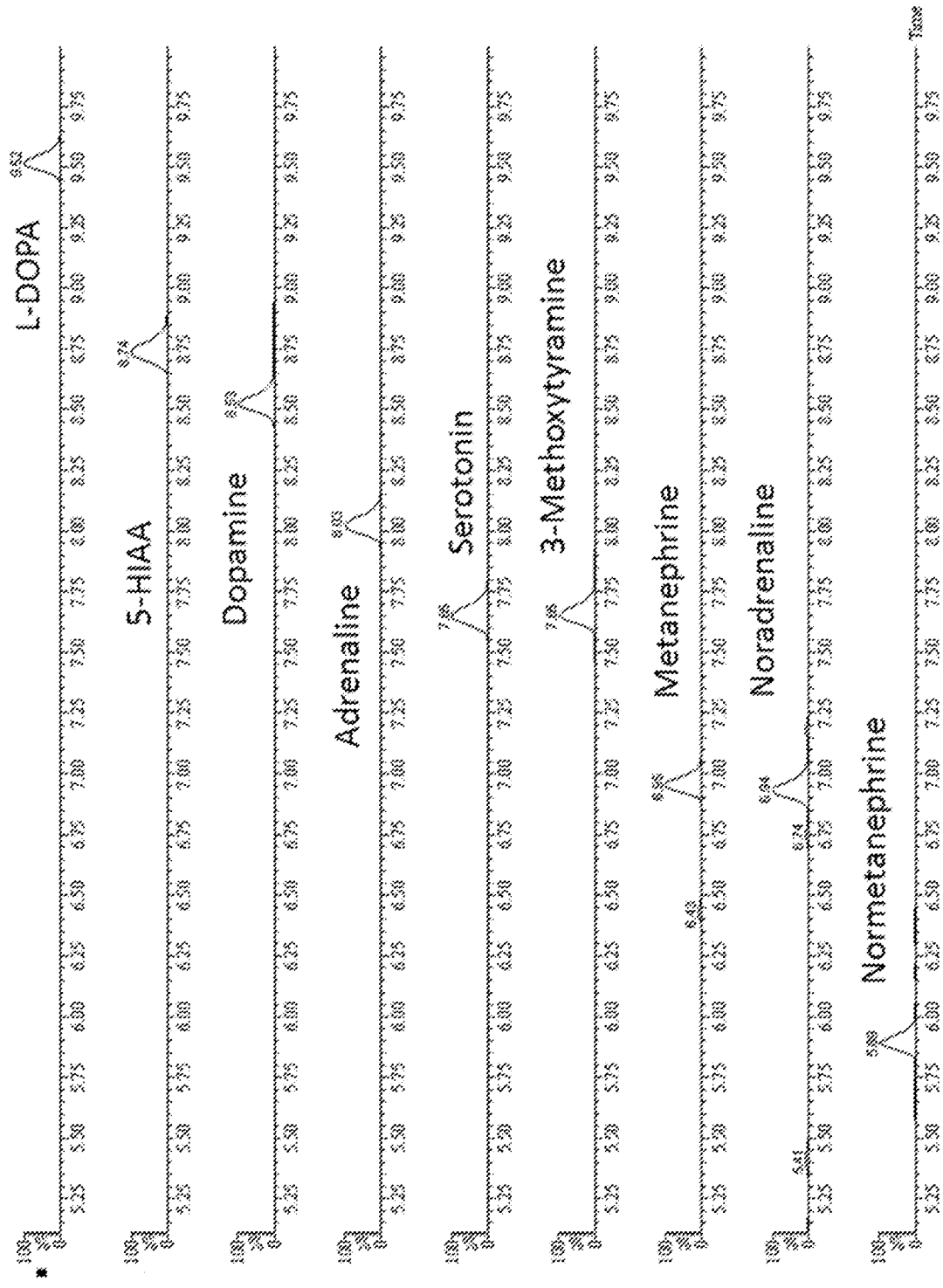

FIG. 3. Representative chromatogram of a urine sample derivatized according to the double derivatization protocol of the invention and subjected to online SPE and LC-MS/MS analysis.

Figure 4:
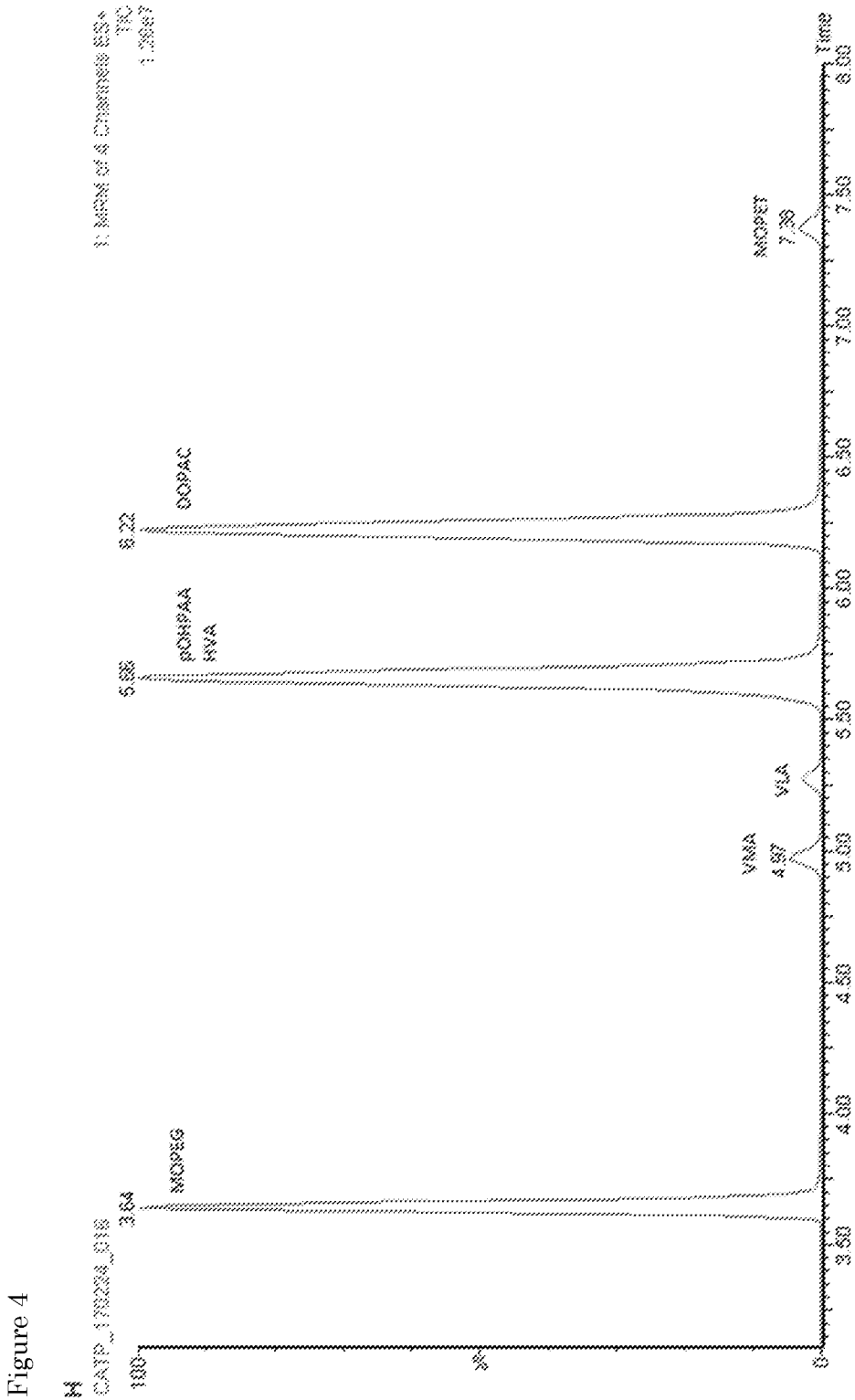

FIG. 4. Typical chromatogram obtained from a urine sample derivatized according to the double derivatization protocol of the invention and subjected to online SPE and LC-MS/MS analysis. For details see Example 2.

Figure 5:
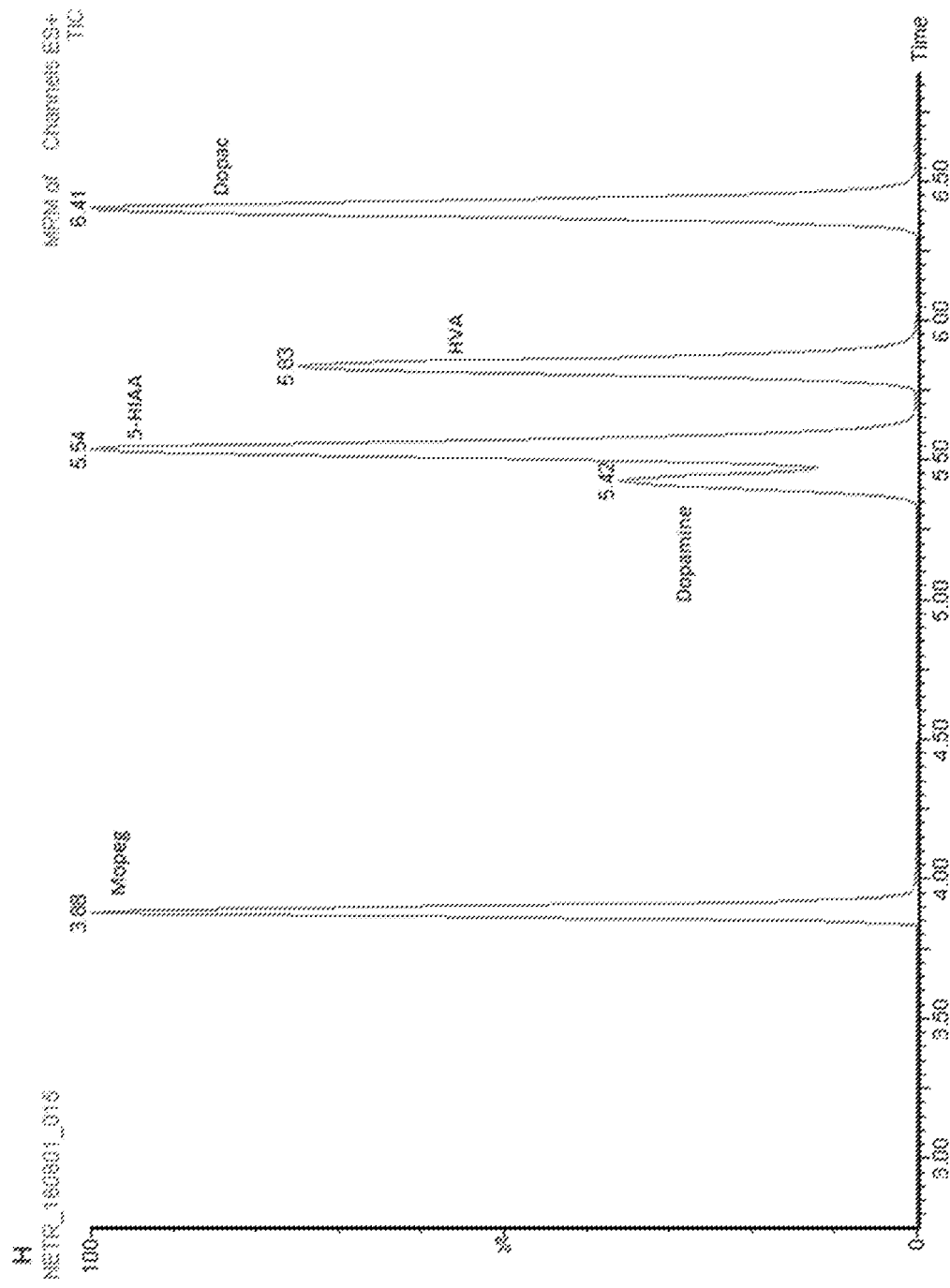

FIG. 5. Typical chromatogram obtained from in a CSF sample derivatized according to the double derivatization protocol of the invention and subjected to online SPE and LC-MS/MS analysis. For details see Example 3.

EXPERIMENTAL SECTION

EXAMPLE 1

Double Derivatization Method in Urine and Analysis of Derivatives

Material and Methods
Reagents

LC-MS grade acetonitrile, isopropanol, methanol, formic acid, and ammonium acetate were purchased from Biosolve BV (Valkenswaard, The Netherlands). Ascorbic acid, clipotassium hydrogen phosphate and hydrochloric acid (32%) were from Merck Millipore (Darmstadt, Germany). Ammonium hydroxide solution (28-30%), 2,2,2-Trilitioroethylamine hydrochloride (TFEA), N-(3-Dimethylaminopropyl)-1V-ethylcarbodiimide hydrochloride (EDC), propionic anhydride, $K_2$EDTA dihydrate, L-DOPA, dopamine-HCl, norepinephrine, epinephrine, 3-methoxytyramine, DL-metanephrine-HCl, DL-normetanephrine-HCl, serotonin, 5-hydroxyindoleacetic acid (5-HIAA) and L-DOPA-d3, all of analytical purity, were purchased from Sigma Aldrich (Missouri, USA). Stable deuterated isotopes for dopamine-d4-HCl, norepinephrine-d6-HCl, serotonin-d4 creatinine sulfate, 5-HIAA-d2 and epinephrine-d3 were from CDN Isotopes (Pointe-Claire, Canada), 3-methoxytyramine-d4-HCl and DL-metanephrine-d3-HCl from Cambridge Isotopes (Massachusetts, USA), and DL-normetanephrine-d3-HCl from Medical Isotopes (New Hampshire, USA). Ultrapure water was produced using an in-house purification system (Merck Millipore, Mass., USA).

Derivatization

Before analysis of samples, aliquots of urine (50 µL), were mixed with 50 µL of internal standard working solution, 200 µL water, 250 µL of 0.5M dipotassium phosphate, 4 mM $K_2$EDTA, pH 8.5 in a 2.0 mL 96-deepwell plate (Greiner Bio-One, Kremsmünster, Austria). Subsequently, 50 µL of 20% (v/v) propionic anhydride in acetonitrile was added and the plate was vortexed for thirty minutes. Thereafter, 100 µL of 0.4M TFEA, 100 µL of 0.4M EDC and water was added To all wells to fill up to a volume of 1.0 mL. The plate was vortexed for thirty minutes and centrifuged for fifteen minutes at 1,500×g. 50 µL of each calibrator and sample was injected into the online SPE LC-MS/MS system, as described below.

LC-MS/MS

Online solid phase extraction (SPE) was performed using the fully automated Spark Holland Symbiosis™ system in eXtraction Liquid Chromatography (XLC) mode as previously described (de Jong, W. H. A. et al. Plasma free metanephrine measurement using automated online solid-phase extraction HPLC tandem mass spectrometry. Clin. Chem. 53, 1684-93 (2007)).

The following cartridges were used for the online spe: Oasis HLB 10×1 mm, 30 µm (Waters). Each cartridge was initially conditioned in the left clamp position with 500 µL acetonitrile, 500 µL of a mixture methanol/isopropanol/acetonitrile/water (1:1:1:1) containing 0.2% formic acid and then equilibrated with 500 µL water, at flow-rates of 5000 µL/min. Sample (100 µL) was aspirated and loaded onto the cartridge with 500 µL water at a flow-rate of 2000 µL/min. The three washing steps were performed with three different solvent compositions: 1) 500 µL 20% methanol, 4 mM ammonium acetate and 0.4% ammonium hydroxide, flow rate of 2500 µL/min, 2) 500 µL 20% methanol, 4 mM ammonium acetate and 0.4% formic acid, flow rate of 2500 µL/min and 3) 250 µL 20% acetonitrile, 4 mM ammonium acetate and 0.4% formic acid, flow rate of 2500 µL/min. After washing, the cartridge was transferred to the right clamp and cortisol and melatonin were eluted by using gradient elution: The cartridge was eluted with the mobile phase starting gradient for 3:00 min. After the elution was performed the right clamp was flushed with 500 µL 40% acetonitrile, 0.1% formic acid at flow rate of 5000 µL/min, 500 µL of a mixture methanol/isopropanol/acetonitrile/water (4:1:1:1) and 0.2% formic acid at flow rate of 5000 µL/min, 500 µL acetonitrile at flow rate of 5000 µL/min and finally 500 µL water at flow rate of 5000 µL/min. A new cartridge was placed in the left clamp allowing the next sample to undergo SPE whilst chromatography was simultaneously being performed on the previous sample. The autosampler was washed with 700 µL 10% acetonitrile, 750 µL 40% acetonitrile, 0.1% formic acid, followed by 750 µL mixture of methanol/isopropanol/acetonitrile/water, 4:2:2:2(v/v) and 0.2% formic acid and then 700 µL 10% acetonitrile again.)

Liquid chromatography was performed on a Phenomenex® Luna Phenyl-Hexyl 2.0×150 mm 3 µm column, with a binary gradient system which consisted of 10 mM ammonium acetate with 0.1% formic acid (eluent A) and 0.1% formic acid in acetonitrile (eluent B). Initial conditions were 80:20 (v/v), eluent A:eluent B, at a flow-rate of 0.3 mL/min followed by a linear increase of eluent B to 55% over 8.5 minutes and then rapid linear increase to 100% B, where it was kept constant for 1.0 minute. Thereafter, flow-rate and proportion of the pumps were returned to the starting conditions and kept constant for a further two minutes. Total run time was 12 minutes.

All analytes were analyzed in positive ionization mode on a Waters® Quattro Premier. Mass spectrometer settings were optimized by tuning in the selective reaction monitoring mode (SRM). The following settings were applied throughout the study: capillary voltage 0.5 kV, desolvation temperature 450° C., desolvation gas flow 1000 L/h, cone gas flow 50 L/h and collision gas flow 0.20 mL/min.

Cone voltage and collision energies were optimized for all analytes and respective transitions and are listed in Table 1. Quantitation was performed by using the peak-area response ratios of the quantifier transitions for the analyte and the corresponding internal standard. Calculations were performed with the Targetlynx™ software (Waters, Milford, USA).

TABLE 1

Mass spectrometer settings for quantifier and qualifier of each compound are listed.

| Segment chromatogram | Compound | Mass precursor-ion (Da) | Mass product-ion (Da) | Cone (V) | Coll. Energy (eV) |
|---|---|---|---|---|---|
| 1 (6-8.8 minutes) | Normetanephrine | 278 | 166 | 20 | 19 |
| | | 278 | 222 | 20 | 12 |
| | Normetanephrine-d3 | 281 | 169 | 20 | 19 |
| | | 281 | 225 | 20 | 12 |
| | Metanephrine | 292 | 180 | 28 | 23 |
| | | 292 | 236 | 28 | 15 |
| | Metanephrine-d3 | 295 | 183 | 28 | 23 |
| | | 295 | 239 | 28 | 15 |
| | Noradrenaline | 320 | 152 | 26 | 29 |
| | | 320 | 208 | 26 | 19 |
| | Noradrenaline-d6 | 326 | 158 | 26 | 29 |
| | | 326 | 214 | 26 | 19 |
| 2 (8.8-10.4 minutes) | 3-Methoxytyramine | 280 | 151 | 22 | 24 |
| | | 280 | 224 | 22 | 13 |
| | 3-Methoxytyramine-d4 | 284 | 155 | 22 | 24 |
| | | 284 | 228 | 22 | 13 |
| | Serotonin | 289 | 160 | 22 | 27 |
| | | 289 | 216 | 22 | 16 |
| | Serotonin-d4 | 293 | 164 | 22 | 27 |
| | | 293 | 220 | 22 | 16 |
| | Adrenaline | 334 | 166 | 30 | 32 |
| | | 334 | 222 | 30 | 22 |
| | Adrenaline-d3 | 337 | 169 | 30 | 32 |
| | | 337 | 225 | 30 | 22 |
| 3 (10.4-11.7 minutes) | Dopamine | 322 | 137 | 20 | 30 |
| | | 322 | 266 | 20 | 12 |
| | Dopamine-d4 | 326 | 141 | 20 | 30 |
| | | 326 | 270 | 20 | 12 |
| | 5-HIAA | 330 | 146 | 28 | 28 |
| | | 330 | 202 | 28 | 14 |
| | 5-HIAA-d2 | 332 | 148 | 28 | 28 |
| | | 332 | 204 | 28 | 14 |
| 4 (11.7-15 minutes) | L-DOPA | 447 | 208 | 22 | 31 |
| | | 447 | 264 | 22 | 21 |
| | L-DOPA-d3 | 450 | 211 | 22 | 31 |
| | | 450 | 267 | 22 | 21 |

EXAMPLE 2

Double Derivatization Method in Urine and Analysis of Derivatives

Material and Methods

Reagents

LC-MS grade acetonitrile, isopropanol, methanol, formic acid, and ammonium acetate were purchased from Biosolve BV (Valkenswaard, The Netherlands). Ascorbic acid, dipotassium hydrogen phosphate and hydrochloric acid (32%) were from Merck Millipore (Darmstadt, Germany). Ammonium hydroxide solution (28-30%), 2,2,2-Trifluoroethylamine hydrochloride (TFEA), N-(3-Dimethylaminopropyl)-N'-ethylcarbothimide hydrochloride (EDC), propionic anhydride, K2EDTA dihydrate, p-Hydroxyphenylacetic acid (pOHPAA), homovanillic acid (HVA), 4-hydroxy-3-methoxyphenylethanol (MOPET), 4-hydroxy-3-methoxymethoxyphenylglycol (MOPEG), vanillylmandelic acid (VMA), vanillyllactic acid (VLA), and 3,4-dihydroxyphenylacetic acid (DOPAC), all of analytical purity, were purchased from Sigma Aldrich (Missouri, USA). Stable labeled isotopes for VMA, DOPAC, pOHPAA, MOPET, and VLA were purchased or synthesized in-house. Ultrapure water was produced using an in-house purification system (Merck Millipore, Mass., USA).

Derivatization

Before analysis of samples, aliquots of urine (50 μL), were mixed with 50 μL of internal standard working solution, 400 μL water, 250 μL of 0.5 M dipotassium phosphate, 4 mM $K_2$EDTA, pH 8.5 in a 2.0 mL 96-deepwell plate (Greiner Bio-One, Kremsmunster, Austria). Subsequently, 50 μL of 20% (v/v) propionic anhydride in acetonitrile was added and the plate was vortexed for thirty minutes. Thereafter, 100 μL of 0.4 M TFEA, 100 μL of 0.4 M EDC and water was added to all wells to fill up to a volume of 1.0mL. The plate was vortexed for thirty. 50 μL of each calibrator and sample was injected into the online SPE LC-MS/MS system, as described below.

LC-MS/MS

Online solid phase extraction (SPE) was performed using the fully automated Spark Holland Symbiosis™ system in eXtraction Liquid Chromatography (XLC) mode as previously described (de Jong, W. H. A. et al. Plasma free metanephrine measurement using automated online solid-phase extraction HPLC tandem mass spectrometry. Clin. Chem. 53, 1684-93 (2007)).

The following cartridges were used for the online SPE: Oasis HLB 10×1 mm, 30 μm (Waters). Each cartridge was initially conditioned in the left clamp position with 500 μL acetonitrile, 500 μL of a mixture methanol/isopropanol/acetonitrile/water (1:1:1:1) containing 0.2% formic acid and then equilibrated with 1000 μL 0.1% formic acid (FA) in water, at flow-rates of 4000 μL/min. Sample (50 μL) was aspirated and loaded onto the cartridge with 600 μL 0.1% FA in water at a flow-rate of 2000 μL/min. The three washing steps were performed with three different solvent compositions: 1) 500 μL 20% methanol, 4 mM ammonium acetate and 0.4% ammonium hydroxide, flow rate of 2500 μL/min, 2) 500 μL 20% methanol, 4 mM ammonium acetate and 0.4% formic acid, flow rate of 2500 μL/min and 3) 250 μL 20% acetonitrile, 4 mM ammonium acetate and 0.4% formic acid, flow rate of 2500 μL/min. After washing, the cartridge was transferred to the right clamp and the derivatives were eluted by using gradient elution: the cartridge was eluted with the mobile phase starting gradient for 3:00 min. After the elution was performed the right clamp was flushed with 750 μL 40% acetonitrile, 0.1% formic acid at flow rate of 5000 μL/min, 750 μL of a mixture methanol/isopropanol/acetonitrile/water (1:1:1:1) and 0.2% formic acid at flow rate of 5000 μL/min,7 50 μL acetonitrile at flow rate of 5000 μL/min and finally 750 μL water at flow rate of 5000 μL/min. A new cartridge was placed in the left clamp allowing the next sample to undergo SPE whilst chromatography was simultaneously being performed on the previous sample. The autosampler was washed with 700 μL 10% acetonitrile, 750 μL 40% acetonitrile, 0.1% formic acid, followed by 750 μL mixture of methanol/isopropanol/acetonitrile/water, 4:2:2:2(v/v) and 0.2% formic acid and then 700 μL 10% acetonitrile again.)

Liquid chromatography was performed on a Phenomenex® Luna Phenyl-Hexyl 2.0×150 mm 3 μm column, with a binary gradient system which consisted of 10 mM ammonium acetate with 0.1% formic acid (eluent A) and 0.1% formic acid in acetonitrile (eluent B). Initial conditions were 75:25 (v/v), eluent A:eluent B, at a flow-rate of 0.3 mL/min followed by a linear increase of eluent B to 45% over 2 minutes, followed by linear increase to 65% B over 4 minutes, and then rapid linear increase to 90% B, where it was kept constant for 1.0 minute. Thereafter, flow-rate and proportion of the pumps were returned to the starting conditions and kept constant for a further two minutes. Total run time was 9.5 minutes.

All analytes were analyzed in positive ionization mode on a Waters® Quattro Premier. Mass spectrometer settings were optimized by tuning in the selective reaction monitoring mode (SRM). The following settings were applied throughout the study: capillary voltage 1.0 kV, desolvation temperature 450° C., desolvation gas flow 1100 L/h, cone gas flow 100 L/h and collision gas flow 0.15 mL/min.

Cone voltage and collision energies were optimized for all analytes and respective transitions and are listed in Table 2. Quantitation was performed by using the peak-area response ratios of the quantifier transitions for the analyte and the corresponding internal standard. Calculations were performed with the Targetlynx™ software (Waters, Milford, USA).

TABLE 2

Mass spectrometer settings for quantifier and qualifier of each compound are listed.

| | Compound name | Precursor (m/z) | Product | Cone (V) | Collision (V) |
|---|---|---|---|---|---|
| 1 | pOHPAA-Quan | 291.00 | 233.95 | 30.00 | 14.00 |
| 2 | pOHPAA-Qual | 291.00 | 106.95 | 30.00 | 26.00 |
| 3 | pOHPAA-d4-Quan | 295.00 | 237.95 | 30.00 | 14.00 |
| 4 | pOHPAA-d4-Qual | 295.00 | 110.95 | 30.00 | 26.00 |
| 5 | Mopet-Quan | 298.00 | 150.95 | 16.00 | 18.00 |
| 6 | Mopet-Qual | 298.00 | 90.95 | 16.00 | 45.00 |
| 7 | Mopet-d3-Quan | 301.00 | 153.95 | 16.00 | 18.00 |
| 8 | Mopet-d3-Qual | 301.00 | 93.95 | 16.00 | 45.00 |
| 9 | HVA-Quan | 337.00 | 136.95 | 16.00 | 28.00 |
| 10 | HVA-Qual | 337.00 | 264.00 | 16.00 | 15.00 |
| 11 | HVA-$^{13}C_6$-Quan | 345.00 | 144.95 | 16.00 | 28.00 |
| 12 | HVA-$^{13}C_6$-Qual | 345.00 | 272.00 | 16.00 | 15.00 |
| 13 | Mopeg-Quan | 258.00 | 166.95 | 14.00 | 13.00 |
| 14 | Mopeg-Qual | 258.00 | 106.95 | 14.00 | 27.00 |
| 15 | Mopeg-$^{13}C_6$-Quan | 264.00 | 172.95 | 14.00 | 13.00 |
| 16 | Mopeg-$^{13}C_6$-Qual | 264.00 | 112.95 | 14.00 | 27.00 |
| 17 | VMA-Quan | 353.00 | 229.95 | 16.00 | 32.00 |
| 18 | VMA-Qual | 353.00 | 109.95 | 16.00 | 45.00 |
| 19 | VMA-d3-Quan | 356.00 | 229.95 | 16.00 | 32.00 |
| 20 | VMA-d3-Qual | 356.00 | 109.95 | 16.00 | 45.00 |
| 21 | Dopac-Quan | 306.00 | 122.95 | 35.00 | 22.00 |
| 22 | Dopac-Qual | 306.00 | 178.95 | 35.00 | 11.00 |
| 23 | Dopac-d3-Quan | 309.00 | 125.95 | 35.00 | 22.00 |
| 24 | Dopac-d3-Qual | 309.00 | 181.95 | 35.00 | 11.00 |
| 25 | VLA-Quan | 350.00 | 176.95 | 25.00 | 18.00 |
| 26 | VLA-Qual | 350.00 | 148.95 | 25.00 | 30.00 |
| 27 | VLA-d3-Quan | 353.00 | 178.95 | 25.00 | 18.00 |
| 28 | VLA-d3-Qual | 353.00 | 150.95 | 25.00 | 30.00 |

EXAMPLE 3

Double Derivatization Method in Cerebrospinal Fluid (CSF) and Analysis of Derivatives.

Reagents

LC-MS grade acetonitrile, isopropanol, methanol, formic acid, and ammonium acetate were purchased from Biosolve BV (Valkenswaard, The Netherlands). Ascorbic acid, dipotassium hydrogen phosphate and hydrochloric acid (32%) were from Merck Millipore (Darmstadt, Germany). Ammonium hydroxide solution (28-30%), 2,2,2-Trifluoroethylamine hydrochloride (TFEA), N-(3-Dimethylaminopropyl)-N'-ethylcarbodiimide hydrochloride (EDC), propionic anhydride, K2EDTA dihydrate, homovanillic acid (HVA), 4-hydroxy-3-methoxy- methoxyphenylglycol (MOPEG), dopamine, 5-HIAA, and 3,4-dihydroxyphenylacetic acid (DOPAC), all of analytical purity, were purchased from Sigma Aldrich (Missouri, USA). Stable labeled isotopes were purchased or synthesized in-house. Ultrapure water was produced using an in-house purification system (Merck Millipore, Massachusetts, USA).

Derivatization

Same as Examples 1 and 2, with the exception that a 100 μL CSF sample, and 350 μL water was used.

LC-MS/MS

Same as in Example 2, but with the MS settings mentioned in table 3.

TABLE 3

Mass spectrometer settings for quantifier and qualifier of each compound are listed.

| | Compound name | Precursor (m/z) | Product (m/z) | Dwell (s) | Cone (V) | Collision (V) |
|---|---|---|---|---|---|---|
| 1 | MOPEG-Quan | 258.00 | 167.00 | 0.100 | 14.00 | 13.00 |
| 2 | MOPEG-Qual | 258.00 | 107.00 | 0.100 | 14.00 | 27.00 |
| 3 | MOPEG-13C6-Quan | 264.00 | 173.00 | 0.100 | 14.00 | 13.00 |
| 4 | MOPEG-13C6-Qual | 264.00 | 113.00 | 0.100 | 14.00 | 27.00 |
| 5 | Dopamine-Quan | 322.00 | 137.00 | 0.060 | 20.00 | 30.00 |
| 6 | Dopamine-Qual | 322.00 | 266.00 | 0.020 | 20.00 | 12.00 |
| 7 | Dopamine-d4-Quan | 326.00 | 141.00 | 0.060 | 20.00 | 30.00 |
| 8 | Dopamine-d4-Qual | 326.00 | 270.00 | 0.020 | 20.00 | 12.00 |
| 9 | 5-HIAA-Quan | 329.00 | 146.00 | 0.060 | 28.00 | 28.00 |
| 10 | 5-HIAA-Qual | 329.00 | 202.00 | 0.020 | 28.00 | 14.00 |
| 11 | 5-HIAA-d2-Quan | 331.00 | 148.00 | 0.060 | 28.00 | 28.00 |
| 12 | 5-HIAA-d2-Qual | 331.00 | 204.00 | 0.020 | 28.00 | 14.00 |
| 13 | HVA-Quan | 337.00 | 137.00 | 0.060 | 16.00 | 28.00 |
| 14 | HVA-Qual | 337.00 | 264.00 | 0.020 | 16.00 | 15.00 |
| 15 | HVA-18O13C6-Quan | 345.00 | 145.00 | 0.060 | 16.00 | 28.00 |
| 16 | HVA-18O13C6-Qual | 345.00 | 272.00 | 0.020 | 16.00 | 15.00 |
| 17 | DOPAC-Quan | 306.00 | 123.00 | 0.100 | 35.00 | 22.00 |
| 18 | DOPAC-Qual | 306.00 | 179.00 | 0.100 | 35.00 | 11.00 |
| 19 | DOPAC-d3-Quan | 309.00 | 126.00 | 0.100 | 35.00 | 22.00 |
| 20 | DOPAC-d3-Qual | 309.00 | 182.00 | 0.100 | 35.00 | 11.00 |

REFERENCES

1. Zhao X-E, Zhu S, Yang H, You J, Song F, Liu Z, et al. Simultaneous determination of amino acid and monoamine neurotransmitters in PC12 cells and rats models of Parkinson's disease using a sensitizing derivatization reagent by UHPLC-MS/MS. J Chromatogr B Analyt Technol Biomed Life Sci. 2015; 995-996C:15-23.

2. Zhang G, Zhang Y, Ji C, McDonald T, Walton J, Groeber E A, et al. Ultra sensitive measurement of endogenous epinephrine and norepinephrine in human plasma by semi-automated SPE-LC-MS/MS. J Chromatogr B Analyt Technol Biomed Life Sci. 2012; 895-896:186-90.

3. Van de Merbel N C, Hendriks G, Imbos R, Tuunainen J, Rouru J, Nikkanen H. Quantitative determination of free and total dopamine in human plasma by LC-MS/MS: the importance of sample preparation. Bioanalysis. 2011; 3:1949-61.

4. Tan B, Lu Z, Dong S, Zhao G, Kuo M-S. Derivatization of the tricarboxylic acid intermediates with O-benzylhydroxylamine for liquid chromatography-tandem mass spectrometry detection. Anal Biochem. 2014; 465:134-47.

5. Ford Q L, Burns J M, Ferry J L. Aqueous in situ derivatization of carboxylic acids by an ionic carbodiimide and 2,2,2-trifluoroethylamine for electron-capture detection. J Chromatogr A. 2007; 1145:241-5.

The invention claimed is:

1. A method for in situ derivatization of at least one biogenic amine, precursor, or metabolite thereof in an aqueous biological sample, the derivatization comprising the steps of:
   (i) contacting said aqueous biological sample with a propionic anhydride/acetonitrile solution in presence of a phosphate buffer having a pH in a range of 7.0 to 9.0, wherein the contacted biological sample comprises a biogenic amine, precursor, or metabolite thereof comprising amine and/or hydroxyl moieties and carboxylic acid moieties, and allowing conversion of the amine and/or hydroxyl moieties of said biogenic amine, precursor, or metabolite thereof to form a reaction mixture comprising a propionyl derivative of said biogenic amine, precursor, or metabolite thereof; followed by
   (ii) adding to the reaction mixture obtained in step (i), a carbodiimide compound and an electrophilic amine-containing compound, and allowing carbodiimide-mediated derivatization of the carboxylic acid moieties of the biogenic amine, precursor, or metabolite thereof.

2. Method according to claim 1, wherein said aqueous biological sample is an isolated aqueous biological sample.

3. Method according to claim 2, wherein the aqueous biological sample is selected from the group consisting of urine, plasma, saliva, CSF, cell lysate and cell culture supernatant.

4. Method according to claim 1, wherein said propionic anhydride/acetonitrile solution is 10-50% v/v propionic anhydride in acetonitrile.

5. Method according to claim 1, wherein the pH of said phosphate buffer is in a range of 8.0 to 8.5.

6. Method according to claim 1, wherein an internal standard is added to the sample prior to performing step (i).

7. Method according to claim 1, wherein step (i) comprises mixing 1 volume of aqueous biological sample, 1 volume of internal standard, and 5 volumes of phosphate buffer, and contacting the mixture with 1 volume of propionic anhydride in acetonitrile.

8. Method according to claim 1, wherein step (ii) comprises adding 2 volumes of the carbodiimide compound and 2 volumes of the electrophilic amine-containing compound to 1 volume of the reaction mixture obtained in step (i).

9. Method according to claim 1, wherein step (ii) comprises adding 2,2,2-trifluroethylamine (TFEA) and N-ethyl-N'-(3-dimethylaminopropyl) carbodiimide (EDC) to the reaction mixture obtained in step (i).

10. Method according to claim 9, wherein TFEA is added prior to EDC.

11. Method according to claim 10, wherein vortexing is performed between adding TFEA and adding EDC.

12. Method according to claim 9, wherein 0.4 M TFEA and 0.4 M EDC are added.

13. Method according to claim 1, further comprising, following step (ii), a centrifugation step.

14. Method according to claim 1, wherein said biogenic amine is selected from the group consisting of L-DOPA, epinephrine, norepinephrine, dopamine, 5-hydroxytryptophan, serotonin, 5-hydroxyindolacetic acid, metanephrine, normetanephrine and 3-methoxytyramine.

15. Method according to claim 1, further comprising detecting at least one derivatized biogenic amine by subjecting the derivatized sample to online solid-phase extraction liquid chromatography tandem mass spectrometry (SPE-LC-MS/MS).

16. Method according to claim 15, wherein said detecting is performed at least one week after derivatization.

* * * * *